United States Patent [19]
Marx

[11] Patent Number: 5,759,169
[45] Date of Patent: Jun. 2, 1998

[54] FIBRIN SEALANT GLUE-GUN

[75] Inventor: Gerard Marx, New York, N.Y.

[73] Assignee: New York Blood Center Inc., New York, N.Y.

[21] Appl. No.: 615,651

[22] Filed: Mar. 13, 1996

[51] Int. Cl.$^6$ .................................................. A61M 37/00
[52] U.S. Cl. ............................ 604/82; 604/191; 606/213; 128/200.21
[58] Field of Search ........................... 604/82, 191, 11, 604/370; 606/213, 214; 128/200.14, 200.21

[56] References Cited

U.S. PATENT DOCUMENTS

| | | |
|---|---|---|
| 2,533,004 | 12/1950 | Ferry et al. |
| 4,359,049 | 11/1982 | Redl et al. |
| 4,631,055 | 12/1986 | Redl et al. |
| 4,735,616 | 4/1988 | Eibl et al. |
| 4,874,368 | 10/1989 | Miller et al. |
| 4,902,281 | 2/1990 | Avoy |
| 4,978,336 | 12/1990 | Capozzi et al. |
| 4,979,942 | 12/1990 | Wolf et al. |
| 5,582,596 | 12/1996 | Fukunaga et al. ............. 604/82 X |

OTHER PUBLICATIONS

Fibrin Sealant Delivery System, *Micromedics, Inc. Brochure*, 2 pages, Jun. 1992.
FibriJet Surgical Sealant Delivery Systems, Undated.
DuoFlo Dispenser Kit, *Hemaedics, Inc. Brochure*, 1 page, 1989.

*Primary Examiner*—Michael Buiz
*Assistant Examiner*—N. Kent Gring
*Attorney, Agent, or Firm*—Amster, Rothstein & Ebenstein

[57] ABSTRACT

An applicator for dispensing a first and a second component of a biological adhesive, such as a fibrin sealant, wherein the applicator comprises a housing having a first dispensing conduit for dispensing the first component and a second dispensing conduit for dispensing the second component. A pressure supply conduit is in communication with the dispensing conduits and both a first reservoir containing the first component, and a second reservoir containing the second component. A first pressure regulator, also in communication with the first reservoir, controls the pressure supplied through the pressure supply conduit to the first reservoir and a second pressure regulator, also in communication with the second reservoir, controls the pressure supplied through the pressure supply conduit to the second reservoir. The pressure regulators may be pressure regulating screws or valves, or they may comprise dispensing conduits having various cross sectional areas or reservoir conduits having various cross sectional areas. The applicator dispenses the first and second components, typically a thrombin solution and a fibrinogen solution, in controlled proportions by adjustment of the pressure regulators.

47 Claims, 4 Drawing Sheets

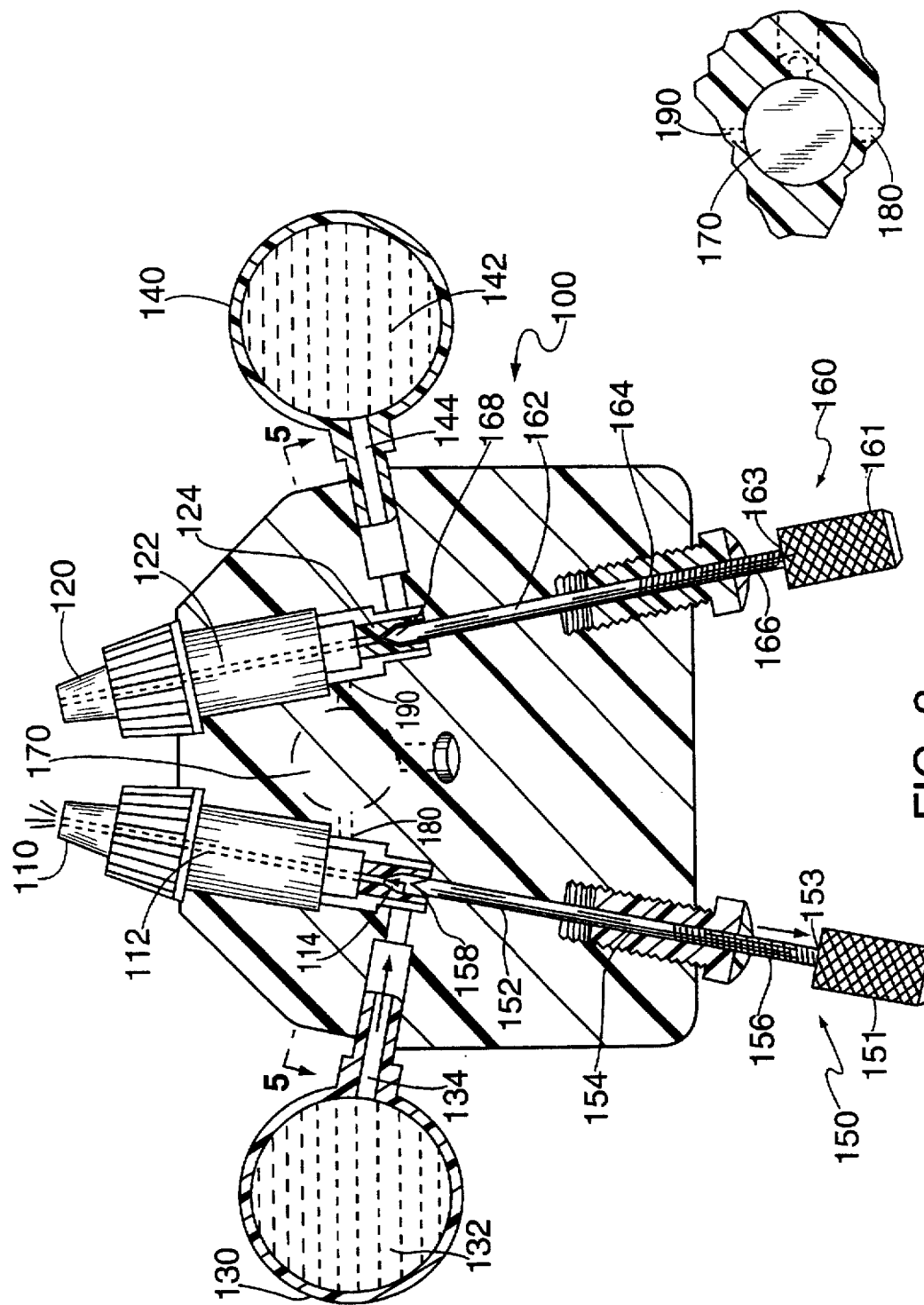

FIBRIN SEALANT GLUE-GUN

BACKGROUND OF THE INVENTION

1. Field of the Invention

The invention relates generally to an applicator for dispensing a first and second component of a biological adhesive and more particularly to an apparatus and method for applying a biological adhesive to tissues or organs for sealing wounds and stopping bleeding or to coat prosthetic devices.

2. Description of Related Art

Biological adhesives, such as fibrin sealants, have been used to seal wounds and stop bleeding. The components of fibrin sealants include a solution containing thrombin and a solution containing fibrinogen. The solution containing thrombin generally has a relative viscosity of approximately 1.0. The solution containing fibrinogen, on the other hand, can have various relative viscosities depending upon the concentration of fibrinogen. Along those lines, U.S. Pat. No. 2,533,004 to Ferry is directed to various fibrin sealants using different concentrations of fibrinogen and thrombin solutions. Accordingly, an applicator must effectively dispense components having various viscosities. Furthermore, due to the varying viscosities of the solutions, as well as the need for varying adhesive properties, the proportion of the thrombin solution dispensed in relation to the dispensed fibrinogen solution must be controllable.

Although various types of applicators for fibrin sealant have previously been used, such prior applicators have failed to incorporate any structure and method for varying the dispensed proportions of the thrombin solution relative to the fibrinogen solution. U.S. Pat. No. 4,735,616 to Eibl et al. is directed to an arrangement for applying a biological adhesive. The Eibl arrangement includes syringe bodies having equal effective strokes yet different cross-sectional areas. Due to the difference in cross-sectional areas of the two syringes, the ratio of fluid in one syringe that is dispensed relative to the amount of fluid in the second syringe that is dispensed does not equal 1. The device does not allow varying proportions of the fluid to be dispensed. In order for different proportions of the fluids to be dispensed, the syringe must be replaced with another syringe having a different cross-sectional area. As such, these earlier devices prove to be quite cumbersome in use.

Furthermore, previous applicators for dispensing a biological adhesive require the manual exertion of a force on the components so that they may be expelled from the applicator. Typically, a manual force is exerted on the components by means of a standard one-way syringe. This type of arrangement is shown in U.S. Pat. Nos. 4,359,049 and 4,631,055 to Redl et al. Although the embodiments of Redl et al. utilize a pressurized gas, the devices disclosed therein requires a manual force to expel the adhesive as the gas is used to merely atomize the adhesive. See U.S. Pat. No. 4,631,055 Col. 3, lines 41–48; U.S. Pat. No. 4,359,049 Col 3, lines 54–57. Manually exerting a force on the components can make application of the adhesive awkward, imprecise, and wasteful.

Similarly, although a syringe-type arrangement is avoided in U.S. Pat. No. 4,902,281 to Avoy, that patent requires a manually exerted force to be applied to the adhesive components. The Avoy patent is directed to the use of a pumping mechanism to expel the adhesive components from the applicator. In order to achieve the desired spray pattern, an abrupt depression of the pumping mechanism must be applied. Like the syringe arrangements, such an applicator is awkward, imprecise, and results in wasted adhesive.

Known devices for applying biological adhesives also suffer from the disadvantage of being difficult to reuse. Once the various components that comprise the adhesive are used up, the supplies must be replenished. In an applicator using a syringe-type arrangement, such as disclosed in the U.S. Patents to Redl et al. discussed above, and in U.S. Pat. No. 4,979,942 to Wolf et al., replenishing the supply of components includes removing a clip which couples the two syringe plungers, detaching the syringes from a form of "Y" connector, removing the syringes from the holder, inserting new syringes, affixing the syringes to the "Y" connector, and replacing the plunger clip. In an application where time is of the essence, such a lengthy replenishing process is impractical and cumbersome.

The reloading procedure in U.S. Pat. No. 4,902,201 to Avoy is similarly inefficient and cumbersome. Replenishing the component solutions involves unlatching the door, opening the housing, removing the spent containers, replacing the containers and closing the housing. Like the replenishing procedure of the syringe-based applicators, this, too, is an involved, time-consuming process.

Users of the known applicators encounter an additional difficulty when replenishing the supply of solutions. If a different combination of components is to be used in the applicator, the applications must be cleaned or, in a syringe-type arrangement, the "Y" connector must be replaced. Cleaning the applicator can be time consuming and replacing parts of the applicator is wasteful and non-economical.

OBJECTS OF THE INVENTION

Thus, it is a primary objective of the present invention to provide a fibrin sealant applicator wherein the dispensed ratio of thrombin solution to fibrinogen solution is variable and which does not require interchanging elements to vary the dispensing ratio.

It is another object of the present invention to provide a fibrin sealant applicator wherein a force other than a manual force is used to expel the adhesive components.

It is yet another object of the present invention to provide a fibrin sealant applicator which is precise and avoids wasting adhesive solutions.

It is still another object of the present invention to provide a fibrin sealant applicator wherein the component solutions are easily replenished without waste.

It is another object of the present invention to provide a fibrin sealant applicator which is reusable with different component solutions.

It is yet another object of the present invention to provide a fibrin sealant applicator which is self-cleaning.

It is yet another object of the present invention to provide a fibrin sealant applicator which dispenses a homogeneous mixture of components.

SUMMARY OF THE INVENTION

In accordance with the aforementioned objects, the present invention includes an applicator for dispensing a first and a second component of a biological adhesive. The biological adhesive may be, but is not limited to, a fibrin sealant. The applicator comprises a housing having a first dispensing conduit for dispensing the first component and a second dispensing conduit for dispensing the second component. A pressure supply conduit is in communication with the dispensing conduits and both a first reservoir containing the first component, and a second reservoir containing the second component. A first pressure regulator, also in communication with the first reservoir, controls the pressure supplied through the pressure supply conduit to the first reservoir and a second pressure regulator, also in communication with the second reservoir, controls the pressure supplied through the pressure supply conduit to said second reservoir. In alternate embodiments, the pressure regulators are pressure regulating screws, valves, dispensing conduits having various cross sectional areas, and reservoir conduits having various cross sectional areas. The first and second components, typically a thrombin solution and a fibrinogen solution, are dispensed in controlled proportions by adjusting the pressure regulators.

BRIEF DESCRIPTION OF THE DRAWINGS

FIG. 3 is an elevated cross-sectional view of the sprayer head in of FIG. 2 along line 3—3;

FIG. 4 is a partial cross-sectional view of the spray of in FIG. 2 along line 4—4.

DETAILED DESCRIPTION OF THE PREFERRED EMBODIMENTS

Figure 1:
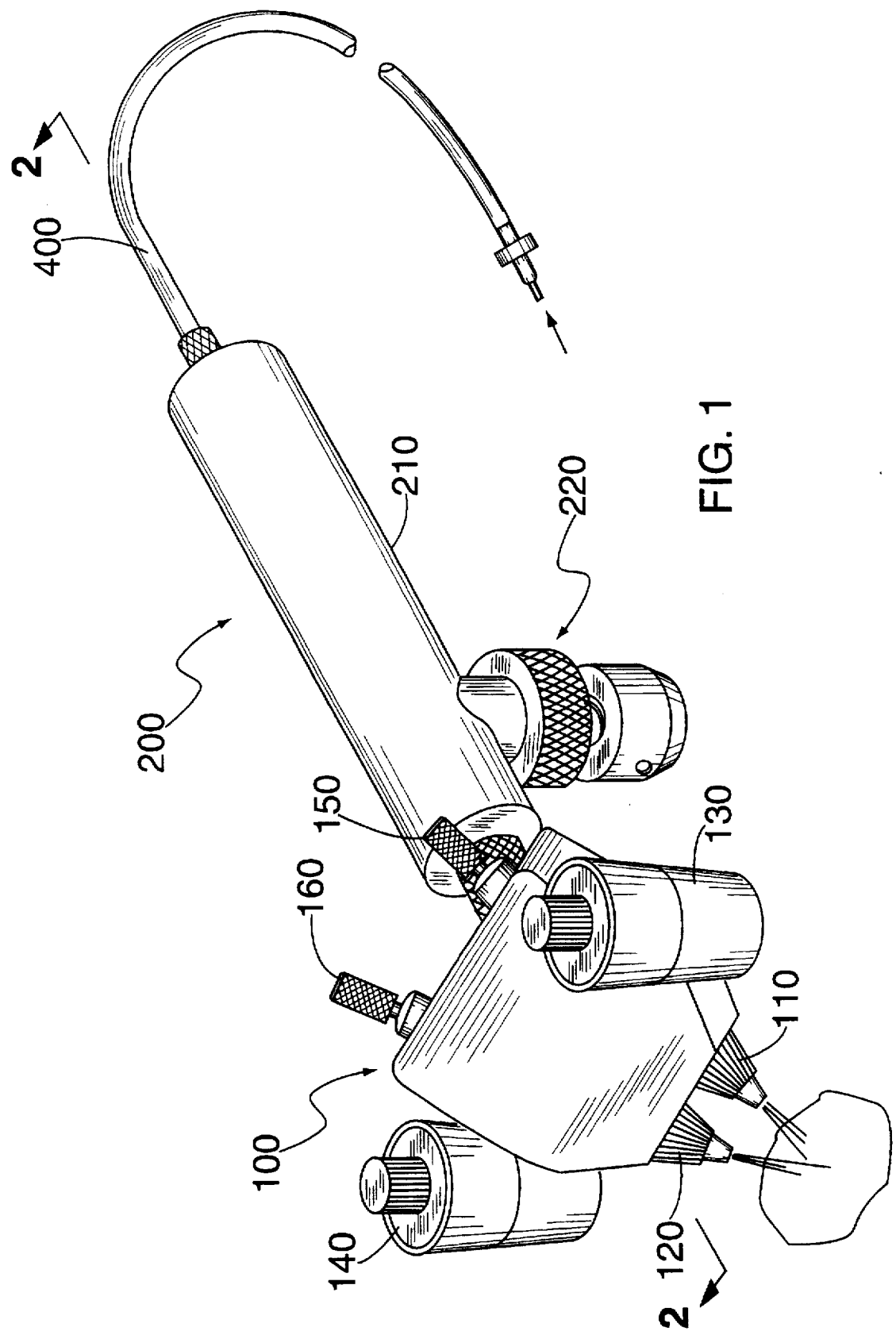
FIG. 1 is an elevated plan view of a preferred embodiment of the applicator of the present invention.

Referring to FIG. 1, an applicator according to one embodiment of the present invention is shown. The applicator consists generally of a spray head 100, a main body 200 and an air supply tube 400, each of these elements being described in greater detail below. The components of the present embodiment are preferably made of medical grade plastics, however it is to be understood that other suitable materials may be used.

The spray head 100 has associated therewith a first reservoir 130 and a second reservoir 140 for containment of biological fluids 132, 142. In the preferred embodiment, the biological fluids 132, 142 are a thrombin solution and a fibrinogen solution, which intermix to form a fibrin sealant. It is to be understood, however, that other biological fluids may be substituted, depending upon the choice of mixture that is to be dispensed.

The spray head 100 also has associated therewith a first nozzle 110 and a second nozzle 120 for directing the spray of the fluids contained in the first and second reservoirs 130, 140, respectively. Because the present invention allows for the application of biological fluids having different viscosities, there is associated with the spray head 100 a first pressure regulator 150 and a second pressure regulator 160.

The main body 200 of the applicator consists of a housing 210 and trigger mechanism 220. While the housing 210 is shown as being cylindrical, it is understood that other shapes that contribute to the ease of gripping and controlling the applicator may be used. As is described in greater detail below, the trigger mechanism 220 controls the flow of air through the main body 200 into the spray head 100. A flow of air is directed to the main body 200 through the air supply tube 400. Although the present embodiment utilizes the flow of air, it should be noted that other gaseous substances, as well as liquids, may be used.

Figure 2:
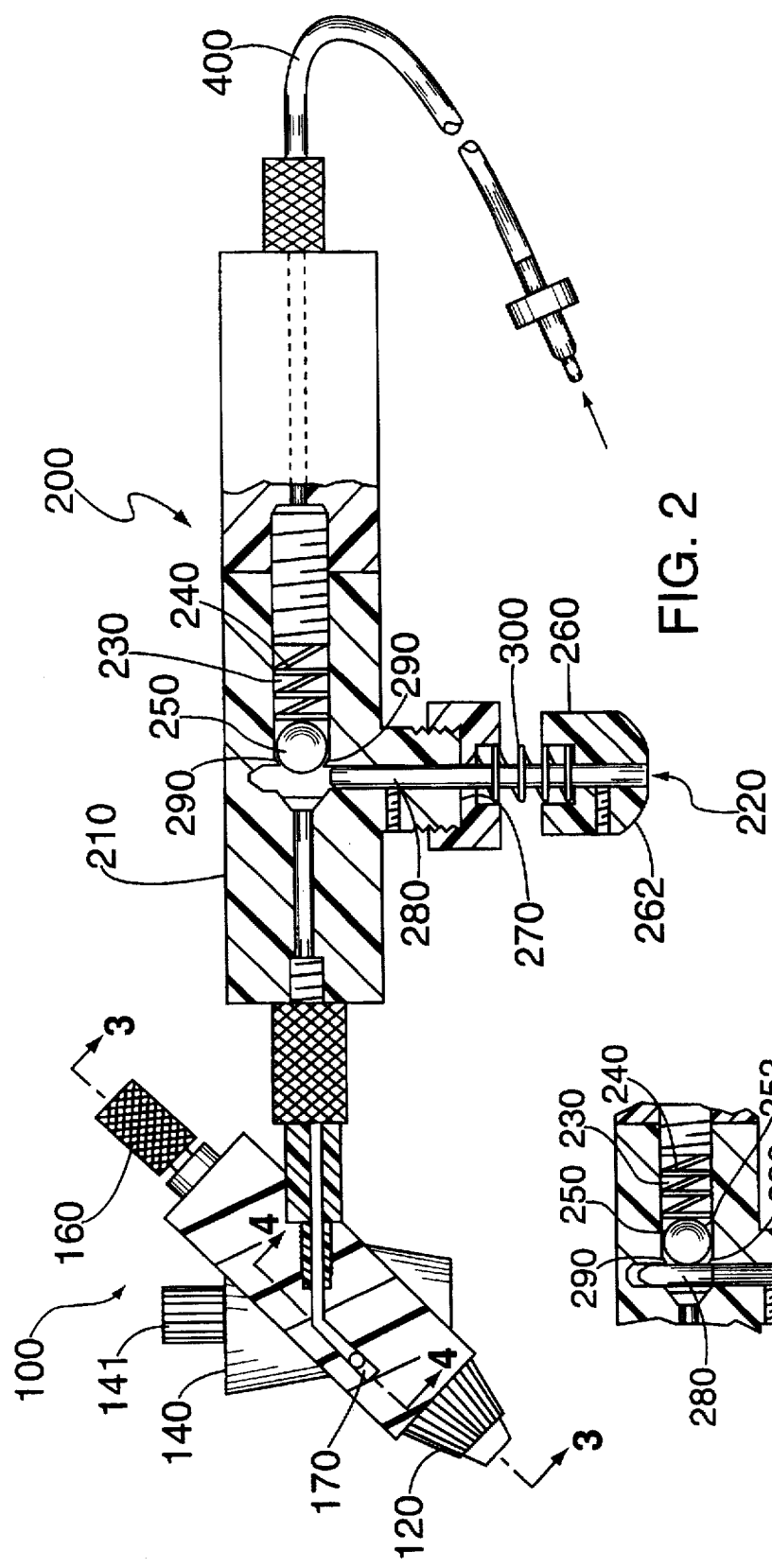
FIG. 2 is a cross-sectional view of the applicator of FIG. 1 along line 2—2.

Referring to FIG. 2, the housing 210 has a bore 230 disposed therethrough. The air supply tube 400 is in communication with the bore 230, thus allowing the flow of air from the air supply tube 400, through the bore 230, and to the spray head 100. The housing 210 has therein a lateral flange 290 extending inward, around the diameter of the bore 230. Spring 240 and bearing 250 are disposed within the bore 230 on the same side of the flange 290 as the air supply tube 400.

FIG. 2 depicts the applicator in an inactivated state with no air flowing therethrough. The trigger mechanism 220 consists of a plunger 260 having a head 262 and a shaft 270. A proximal end 280 of the shaft 270 extends into the body housing 210 and terminates adjacent to the bearing 250. Thus, the proximal end 280 does not interfere with the spring 240 forcing the bearing 250 into contact with the lateral flange 290 of the body housing 210. Because the diameter of the bore 230 at the point of the lateral flange 290 is smaller than the diameter of the bearing 250, a seal is created when the bearing 250 engages the flange 290. Therefore, the flow of air is prevented. The trigger mechanism 220 is maintained in an inactivated state by a spring 300.

Figure 2A:
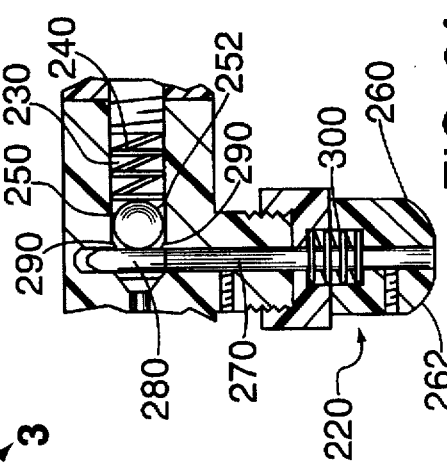
FIG. 2A is a cross-sectional view of the trigger mechanism of the applicator of FIGS. 1 and 2, showing the trigger mechanism in an activated state.
Figure 5:
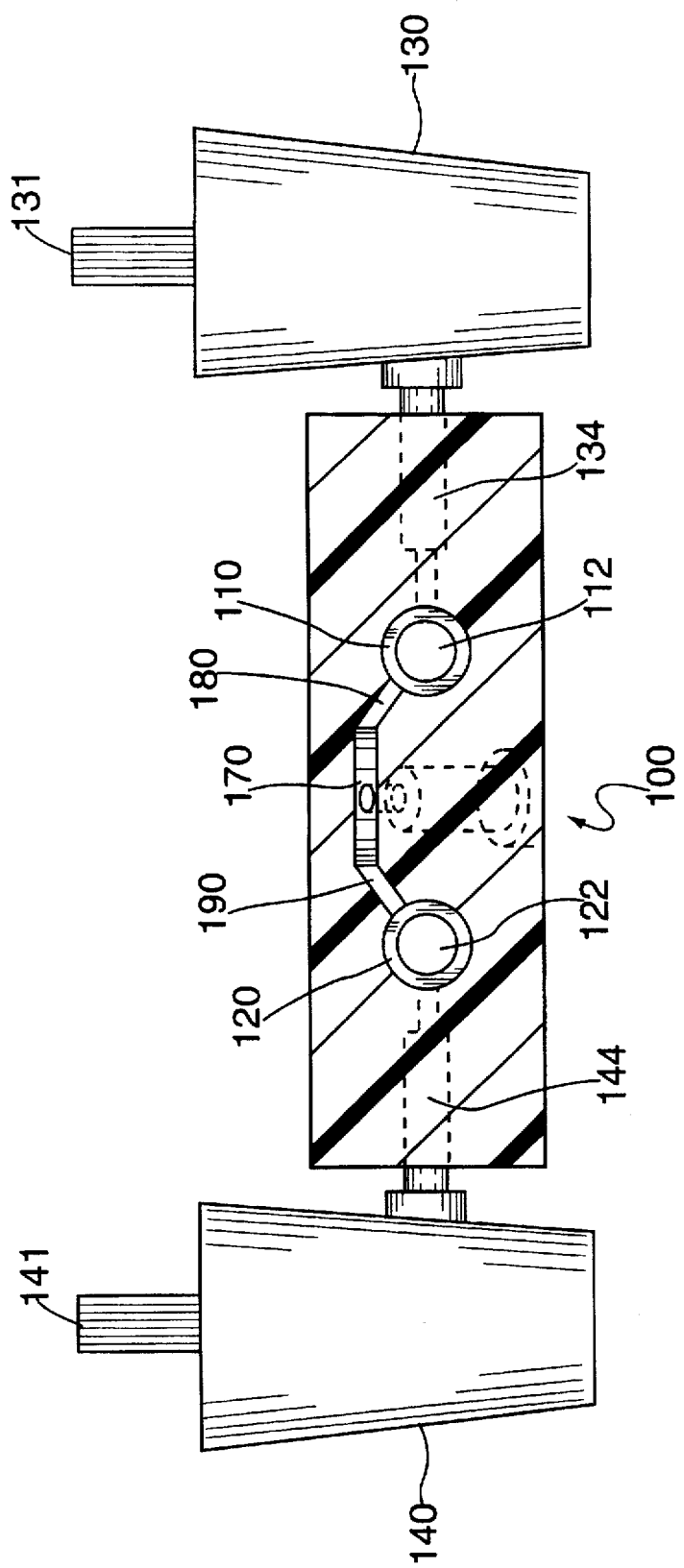
FIG. 5 is a cross-sectional view of the sprayer head of FIG. 3 along line 5—5.

Referring now to FIG. 2A, the trigger mechanism 220 in an activated state is illustrated. By applying a force to the plunger head 262 that is parallel to the shaft 270, the spring 300 is compressed, and the shaft 270 is forced further into the housing 210. As the shaft 270 enters the housing 210, the proximal end 280 slidably engages the bearing 250 and forces the bearing 250 away from the flange 290, thereby compressing spring 240. The proximal end 280 of the shaft 270 is preferably conical in shape thereby contributing to the ease with which the bearing 250 is urged away from the flange 290. Because the outside diameter of the bearing 250 and the outside diameter of the end 280 of the shaft 270 are smaller than the diameter of the bore 230, a gap 252 is created. Thus, air flows from the air supply tube 400, into the bore 230, through the gap 252, and into the spray head 100. When the force applied to the plunger 262 is removed, the spring 300 urges the plunger 260 away from the body housing 210, thereby withdrawing the shaft 270 from the bore 230. The spring 240, as well as the pressure of the flowing air, forces the bearing 250 back into engagement with the flange 290, thereby returning the applicator to the inactivated state as depicted in FIG. 2. Although the present invention has been described with a particular trigger mechanism, it is understood that other similar mechanisms may be employed.

Referring to FIG. 3, there is illustrated in greater detail the spray head 100. A first reservoir 130 and a second 140 reservoir for storing a first biological fluid 132 and a second biological fluid 142 are affixed to the spray head 100. The reservoirs 130, 140 are respectively in communication with nozzle bores 112, 122 via conduits 134, 144. The reservoirs 130, 140 may be permanently affixed to the conduits 134, 144 or, alternatively, the reservoirs 130, 140 may be provided with a luer or other mechanical interfit connection. If the reservoirs 130, 140 utilize a luer mechanism, whether it be a male fitting or a female fitting, the conduits 134, 144 would have a corresponding structure for engaging therewith.

Although the present embodiment according to the claimed invention depicts a certain form of reservoir, it is to be understood that the applicator could be fitted with any of a number of different reservoirs, including, without limitation, syringes, bags or tubing. Furthermore, although the present embodiment according to the claimed invention has but two reservoirs, it is to be understood that additional reservoirs containing other solutions, such as is disclosed in Applicant's co-pending U.S. patent applications Ser. Nos. 08/465,888, 08/459,345, and 08/460,534, herein incorporated by reference, may be similarly incorporated.

When the trigger mechanism 220 is in an activated state, the air flows from the air supply tube 400, through the housing 210, and into the spray head 100 via a main conduit 170. The air travels from the main conduit 170 through a first conduit 180 and into a first nozzle bore 112 disposed in a first nozzle 110. The air also travels from the main conduit 170 through a second conduit 190 and into a second nozzle bore 122 disposed in the second nozzle 120. The air then exits each of the nozzles 110, 120 to the area of lowest pressure—the external environs. The flow of the air through the first and second conduits 180, 190 and through the first and second bores 112, 122 creates regions of low pressure at each of the proximal ends 114, 124 of the nozzle bores 112, 122. The nozzles 110, 120 are preferably adjustable so that the angle at which the components of the adhesive are dispensed may be adjustable, thereby allowing the user to adjust the focal point of the component spray.

FIG. 3 also illustrates a first pressure regulator screw 150. The pressure regulator screw 150 is generally partially disposed within a bore 155 in the spray head 100. The bore 155 and, therefore, the screw 150, is in linear alignment with the first nozzle bore 112. The pressure regulator screw 150 generally comprises a head 151 affixed to the distal end 153 of a shaft 152. 152. The pressure regulator screw shaft 152 has thereon threads 156 for engagement with grooves 154 within the screw bore 155.

Similarly, FIG. 3 also illustrates a second pressure regulator screw 160. This pressure regulator screw 160 is generally partially disposed within a bore 165 in the spray head 100. The bore 165 and, therefore, the screw 160, is in linear alignment with the second nozzle bore 122. This pressure regulator screw 160, like the one 150 previously described, generally comprises a head 161 affixed to the distal end 163 of a shaft 162. This pressure regulator screw shaft 162 similarly has thereon threads 166 for engagement with grooves 164 within the screw bore 165.

FIG. 3 illustrates a pressure regulator screw 150 that has had a counterclockwise torque applied thereto. By applying a counterclockwise torque to the head 151 perpendicular to the shaft 152, the screw 150 is disengaged from the nozzle bore 112. The pressure regulator screw 150 is depicted with the proximal end 158 of the shaft disengaged from the proximal end 114 of the nozzle bore 112. The area of low pressure caused by the flow of the gas through bore 112 causes a biological fluid 132 contained in reservoir 130 to be drawn out through the conduit 134 and into the bore 112. The biological fluid 132 is then expelled from the apparatus through the nozzle 110. As shown in this preferred embodiment, the proximal end 158 of the pressure regulator screw 150 is conical in shape so to be engageable with the proximal end 114 of the bore 112, the proximal end 114 being conical in shape.

FIG. 3 also illustrates a pressure regulator screw 160 that has had a clockwise torque applied thereto. By applying a clockwise torque to the head 161 that is perpendicular to the shaft 162, the shaft 162 may be further disposed within the spray head 100 such that the proximal end 168 of the screw 160 engages with and closes off the proximal end 124 of the nozzle bore 122. Like the first pressure regulator screw 150, the proximal end 168 of the second pressure regulator screw 160 is conical in shape so to be engageable with the proximal end 124 of the bore 122, the proximal end 124 being conical in shape.

The second pressure regulator screw 160 is depicted fully disposed within spray head 100 such that the proximal end 168 is fully engaged with the proximal end 124 of the bore 122. Complete engagement of the proximal end 168 of the shaft with the proximal end 124 of the bore prevents the biological fluid 142 contained in the reservoir 140 from flowing through the bore 122.

Although pressure regulator screw 150 is depicted in a fully disengaged state and pressure regulator screw 160 is depicted in a fully engaged state, intermediate positions are possible. By rotating the pressure regulator screws 150, 160, shafts 152, 162 may be selectively positioned within the screw bores 155, 165 such that the proximal end 158, 168 of the shafts are in partial engagement with the proximal ends 114, 124 of the nozzle bores. Such selective positioning of the pressure regulator screws 150, 160 alter the pressure created by the flow of air through the bores 112, 122 and, consequently, alters the amount of flow of biological fluid 132, 142, from the reservoirs 130, 140. Because each reservoir 130, 140 has associated therewith an independent pressure regulator screw 150, 160, the applicator may dispense the first and second biological fluids 132, 142 in different proportions.

In an alternative embodiment, nozzle bores having different diameters may account for components having different viscosities. Increasing the diameter of a nozzle bore creates a greater pressure differential at the bore's proximal end. The greater pressure differential exerts a greater force on the corresponding component, thereby drawing the component out of the reservoir at an increased rate. Conversely, decreasing the diameter of a nozzle bore reduces the force exerted on a component and decreases the rate at which the component is drawn out of the reservoir. Consequently, components with different relative viscosities may be dispensed in different ratios with respect to each other.

In another alternative embodiment, reservoir conduits having different diameters may allow for the components to be dispensed in different ratios. A larger reservoir conduit allows the component contained therein to flow more freely while a smaller reservoir conduit restricts the flow of the component contained therein. Again, the applicator dispenses different ratios of components having different relative viscosities.

In the present embodiment, the dispensing ratio of the first biological fluid 132 to the second biological fluid 142 ranges generally from 1 to 1 through 1 to 10. Thus, this embodiment is capable of dispensing a first fluid having a relative viscosity of 1.0 and a second fluid having a relative viscosity of 1.0 during a given application and dispensing a first fluid having a relative viscosity of 1.0 and a second fluid having a relative viscosity of 20 during another application.

Regardless of the actual component fluids 132, 142 used, the present embodiment achieves thorough intermixing of the fluids 132, 142 and a homogeneous spray. The applicator delivers a homogeneous spray because a controllable force, other than a manual force, is used to force the fluids 132, 142 from the reservoirs 130, 140 as well as atomize them upon being dispensed. In the present embodiment, air pressure in the range of 25 to 30 pounds per square inch is used although alternative embodiments according to the present invention may use aerosol pressure. By controlling the force as described above, the applicator can deliver a slurry or suspension of particles. Furthermore, the present embodiment has the ability achieve such mixtures of particles ranging in size from at least 0.1 to at least 100 microns. Additionally, these may be regular particles, including, without limitation, spherical proteins or polysaccharidic microbeads or liposomes, or irregular particles, including, without limitation, C18 resin or suspensions of cultured cells such as fibroblasts.

Reuse of the present embodiment is both efficient and economical and may be done in a sterile manner. By using a first nozzle 110 and a second nozzle 120, intermixing of the component fluids 132, 142 occurs external to the applicator. Therefore, the present arrangement avoids clogging. Furthermore, by using an external pressure supply to expel the component fluids 132, 142, virtually all of the fluid 132, 142 is drawn out of the reservoirs 130, 140 and forced out of the applicator. If fluid 132, 142 were to remain attached to either the nozzle bores 112, 122 or the conduits 134, 144, valves 131, 141 on the reservoirs 130, 140 could be opened (or in an alternative embodiment, the reservoirs removed) and pressurized air forced through the applicator. The forced air, with the reservoirs 130, 140 empty, cleans the internal applicator mechanisms thoroughly.

An alternative embodiment of the present invention (not shown) is a modification of the preferred embodiment for use in laproscopic surgery. The modifications to the preferred embodiment include elongating the spray head and reservoirs such that they are tubular and fit within an incision. Alternatively, just the nozzles are elongated so that they are tubular and fit within an incision. The trigger mechanism, as well as the pressure supply, remain outside the patient's body.

Although this invention has been described in terms of certain preferred embodiments, other embodiments that are apparent to those of ordinary skill in the art are also intended to be within the scope of this invention. Accordingly, the scope of the present invention is intended to be limited only by the claims appended hereto.

I claim:

1. An applicator for creating a homogeneous film coating of a biological adhesive, the adhesive comprising a first component and a second component, the applicator comprising:
   (a) a housing having a first dispensing conduit for dispensing said first component and a second dispensing conduit for dispensing said second component;
   (b) a pressure supply conduit in communication with said dispensing conduits;
   (c) a first reservoir containing said first component, said first reservoir being in communication with said first dispensing conduit;
   (d) a second reservoir containing said second component, said second reservoir being in communication with said second dispensing conduit;
   (e) a first pressure regulator in communication with said first reservoir for controlling pressure supplied through said pressure supply conduit to said first reservoir; and
   (f) a second pressure regulator in communication with said second reservoir for controlling pressure supplied through said pressure supply conduit to said second reservoir.

2. The applicator of claim 1 wherein said first pressure regulator comprises an orifice having a predetermined cross sectional area.

3. The applicator of claim 2 wherein said second pressure regulator comprises a second orifice having a second cross sectional area such that said first cross sectional area compared to said second cross sectional area is a predetermined ratio such that a pressure exerted on said first component differs from pressure on said second component.

4. The applicator of claim 1 wherein said first dispensing conduit has a predetermined first cross sectional area.

5. The applicator of claim 4 wherein said second dispensing conduit has a second cross sectional area, wherein said first cross sectional area compared to said second cross sectional area is a predetermined ratio such that a pressure exerted on said first component differs from pressure exerted on said second component.

6. The applicator of claim 1 wherein said first dispensing conduit for dispensing said first component and said second dispensing conduit for dispensing said second component are separate, so that said components intermix external to said applicator.

7. The applicator of claim 6 further comprising a first nozzle affixed to said housing and disposed about said first dispensing conduit, and a second nozzle affixed to said housing and disposed about said second dispensing conduit.

8. The applicator of claim 7 wherein said first pressure regulator comprises a pressure regulating screw, and wherein said second pressure regulator comprises a second pressure regulating screw.

9. The applicator of claim 7 wherein said first pressure regulator comprises a pressure regulating valve, and wherein said second pressure regulator comprises a pressure regulating valve.

10. The applicator of claim 9 wherein said first pressure regulating valve is interposed between said first reservoir and the environs external to said applicator and said second pressure regulating valve is interposed between said second reservoir and the environs external to said applicator.

11. The applicator of claim 9 wherein said first pressure regulating valve and said second pressure regulating valve are interposed between said pressure supply and the environs external to said applicator.

12. The applicator of claim 1 wherein said pressure supply conduit is in communication with a pressurized gas.

13. The applicator of claim 1 wherein said first component is a thrombin solution and said second component is a fibrinogen solution, whereby said adhesive is a fibrin sealant.

14. The applicator of claim 1 wherein said first component has a relative viscosity in the range of 1 to 10, inclusive, and said second component has a relative viscosity in the range of 1 to 10, inclusive.

15. The applicator of claim 1 wherein said adhesive comprises a predetermined ratio of said first component to said second component.

16. The applicator of claim 15 wherein said predetermined ratio is in the range of 1:1 to 1:10, inclusive.

17. The applicator of claim 1 wherein said first component has a relative viscosity in the range of 1 to 20, inclusive, and said second component has a relative viscosity in the range of 1 to 20, inclusive.

18. An applicator for dispensing a first component of a biological adhesive contained in a first storage means and a second component contained in a second storage means, the applicator comprising:
   (a) a pressure supply means in communication with said storage means for creating a first and second pressure differential, said first pressure differential existing between said first storage means and said pressure supply means so that said first component is forced out of said first storage means, and said second pressure differential existing between said second storage means and said pressure supply means so that said second component is forced out of said second storage means;
   (b) a first pressure regulating means in communication with said pressure supply means for regulating said first pressure differential; and (c) a second pressure regulating means in communication with said pressure supply means for regulating said second pressure differential.

19. The applicator of claim 18 wherein said first pressure regulating means is in communication with said first storage means and said second pressure regulating means is in communication with said second storage means.

20. The applicator of claim 18 further comprising a first dispensing means in communication with said first storage means for directing said first component out of said applicator, and a second dispensing means in communication with said second storage means for directing said second component out of said applicator.

21. The applicator of claim 20, wherein said first dispensing means and said second dispensing means are affixed to said applicator.

22. The applicator of claim 20 wherein said first dispensing means has a predetermined first cross sectional area.

23. The applicator of claim 22 wherein said second dispensing means has a second cross sectional area such that said first cross sectional area compared to said second cross sectional area is a predetermined ratio such that a pressure exerted on said first component differs from pressure on said second component.

24. The applicator of claim 18 wherein said first pressure regulating means comprises an orifice having a predetermined cross sectional area.

25. An applicator for dispensing a first component of a biological adhesive contained in a first storage means and a second component contained in a second storage means, the applicator comprising:
 (a) a pressure supply means in communication with said storage means for creating a first and second pressure differential, said first pressure differential existing between said first storage means and said pressure supply means so that said first component is forced out of said first storage means, and said second pressure differential existing between said second storage means and said pressure supply means so that said second component is forced out of said second storage means;
 (b) a first pressure regulating means in communication with said pressure supply means for regulating said first pressure differential; and
 (c) a second pressure regulating means in communication with said pressure supply means for regulating said second pressure differential;
 said first pressure regulating means comprising a pressure regulating screw, and said second pressure regulating means comprising a pressure regulating screw.

26. The applicator of claim 25 wherein said first component has a first relative viscosity and said second component has a second relative viscosity, and said first pressure differential and said second pressure differential being such that said first component and said second component are dispensed in a ratio of 1:1.

27. The applicator of claim 25 wherein said pressure supply means is pressurized gas.

28. An applicator for dispensing a first component of a biological adhesive contained in a first storage means and a second component contained in a second storage means, the applicator comprising:
 (a) a pressure supply means in communication with said storage means for creating a first and second pressure differential, said first pressure differential existing between said first storage means and said pressure supply means so that said first component is forced out of said first storage means, and said second pressure differential existing between said second storage means and said pressure supply means so that said second component is forced out of said second storage means;
 (b) a first pressure regulating means in communication with said pressure supply means for regulating said first pressure differential; and
 (c) a second pressure regulating means in communication with said pressure supply means for regulating said second pressure differential;
 said first pressure regulating means comprising a pressure regulating valve and said second pressure regulating means comprising a pressure regulating valve.

29. The applicator of claim 28 wherein said first pressure regulating means is in communication with said first storage means and said second pressure regulating means is in communication with said second storage means.

30. The applicator of claim 28 further comprising a first dispensing means in communication with said first storage means for directing said first component out of said applicator, and a second dispensing means in communication with said second storage means for directing said second component out of said applicator.

31. The applicator of claim 30, wherein said first dispensing means and said second dispensing means are affixed to said applicator.

32. The applicator of claim 30, wherein said first dispensing means has a predetermined first cross sectional area.

33. The applicator of claim 32, wherein said second dispensing means has a second cross sectional area such that said first cross sectional area compared to said second cross sectional area is a predetermined ratio such that a pressure exerted on said first component differs from pressure on said second component.

34. The applicator of claim 28 wherein said first component has a first relative viscosity and said second component has a second relative viscosity, and said first pressure differential and said second pressure differential being such that said first component and said second component are dispensed in a ratio of 1:1.

35. The applicator of claim 28 wherein said pressure supply means is pressurized gas.

36. An applicator for dispensing a first component of a biological adhesive contained in a first storage means and a second component contained in a second storage means, the applicator comprising:
 (a) a pressure supply means in communication with said storage means for creating a first and second pressure differential, said first pressure differential existing between said first storage means and said pressure supply means so that said first component is forced out of said first storage means, and said second pressure differential existing between said second storage means and said pressure supply means so that said second component is forced out of said second storage means;
 (b) a first pressure regulating means in communication with said pressure supply means for regulating said first pressure differential; and
 (c) a second pressure regulating means in communication with said pressure su poly means for regulating said second pressure differential;
 said first pressure regulating means comprising an orifice having a predetermined cross sectional area, and said second pressure regulating means comprising a second orifice having a second cross sectional area, wherein said first cross sectional area compared to said second cross sectional area is a predetermined ratio such that a pressure exerted on said first component differs from pressure on said second component.

37. A method of creating a homogeneous film coating of a biological adhesive on a tissue or prosthetic surface, and the like, the adhesive comprising a first component stored in a first container and a second component stored in a second container, the method comprising the steps of:
  (a) simultaneously exerting a first force on said first component thereby forcing said first component out of said first container and exerting a second force on said second component thereby forcing said second component out of said second container;
  (b) regulating said first force and said second force so that the resulting adhesive comprises a predetermined ratio of said first component to said second component;
  (c) dispensing said first component and said second component in said predetermined ratio.

38. The method of claim 37 wherein the step of dispensing said components includes dispensing said first component separately from said second component.

39. The method of claim 38 further comprising the step of adjusting the dispensing angle of said first component and adjusting the dispensing angle of said second component.

40. An applicator for creating a homogeneous film coating of a biological adhesive, the adhesive comprising a first component and a second component, the applicator comprising:
  (a) a housing having a first dispensing conduit for dispensing said first component and a second dispensing conduit for dispensing said second component;
  (b) a pressure supply conduit in communication with said dispensing conduits;
  (c) a first reservoir containing said first component, said first reservoir being in communication with said first dispensing conduit;
  (d) a second reservoir containing said second component, said second reservoir being in communication with said second dispensing conduit;
  (e) a first pressure regulator in communication with said first reservoir for controlling pressure supplied through said pressure supply conduit to said first reservoir; and
  (f) a second pressure regulator in communication with said second reservoir for controlling pressure supplied through said pressure supply conduit to said second reservoir;
    said first pressure regulator comprising an orifice having a predetermined cross sectional area, and said second pressure regulator comprising a second orifice having a second cross sectional area such that said first cross sectional area compared to said second cross sectional area is a predetermined ratio such that a pressure exerted on said first component differs from pressure on said second component.

41. An applicator for creating a homogeneous film coating of a biological adhesive, the adhesive comprising a first component and a second component, the applicator comprising:
  (a) a housing having a first dispensing conduit for dispensing said first component and a second dispensing conduit for dispensing said second component;
  (b) a pressure supply conduit in communication with said dispensing conduits;
  (c) a first reservoir containing said first component, said first reservoir being in communication with said first dispensing conduit;
  (d) a second reservoir containing said second component, said second reservoir being in communication with said second dispensing conduit;
  (e) a first pressure regulator in communication with said first reservoir for controlling pressure supplied through said pressure supply conduit to said first reservoir; and
  (f) a second pressure regulator in communication with said second reservoir for controlling pressure supplied through said pressure supply conduit to said second reservoir; said first pressure regulator comprising an orifice having a predetermined cross sectional area;
    said first dispensing conduit having a predetermined first cross sectional area, and said second dispensing conduit having a second cross sectional area, wherein said first cross sectional area compared to said second cross sectional area is a predetermined ratio such that a pressure exerted on said first component differs from pressure exerted on said second component.

42. An applicator for creating a homogeneous film coating of a biological adhesive, the adhesive comprising a first component and a second component, the applicator comprising:
  (a) a housing having a first dispensing conduit for dispensing said first component and a second dispensing conduit for dispensing said second component;
  (b) a pressure supply conduit in communication with said dispensing conduits;
  (c) a first reservoir containing said first component, said first reservoir being in communication with said first dispensing conduit;
  (d) a second reservoir containing said second component, said second reservoir being in communication with said second dispensing conduit;
  (e) a first pressure regulator in communication with said first reservoir for controlling pressure supplied through said pressure supply conduit to said first reservoir; and
  (f) a second pressure regulator in communication with said second reservoir for controlling pressure supplied through said pressure supply conduit to said second reservoir; said first pressure regulator comprising an orifice having a predetermined cross sectional area;
    said first dispensing conduit for dispensing said first component and said second dispensing conduit for dispensing said second component being separate, so that said components intermix external to said applicator;
    said applicator further comprising a first nozzle affixed to said housing and disposed about said first dispensing conduit, and a second nozzle affixed to said housing and disposed about said second dispensing conduit;
    said first pressure regulator comprising a pressure regulating screw, and wherein said second pressure regulator comprising a second pressure regulating screw.

43. The applicator of claim 42 wherein said first pressure regulating screw is interposed between said first reservoir and the environs external to said applicator and said second pressure regulating screw is interposed between said second reservoir and the environs external to said applicator.

44. The applicator of claim 42 wherein said first pressure regulating screw and said second pressure regulating screw are interposed between said pressure supply and the environs external to said applicator.

45. An applicator for creating a homogeneous film coating of a biological adhesive, the adhesive comprising a first component and a second component, the applicator comprising:

(a) a housing having a first dispensing conduit for dispensing said first component and a second dispensing conduit for dispensing said second component;

(b) a pressure supply conduit in communication with said dispensing conduits;

(c) a first reservoir containing said first component, said first reservoir being in communication with said first dispensing conduit;

(d) a second reservoir containing said second component, said second reservoir being in communication with said second dispensing conduit;

(e) a first pressure regulator in communication with said first reservoir for controlling pressure supplied through said pressure supply conduit to said first reservoir; and (f) a second pressure regulator in communication with said second reservoir for controlling pressure supplied through said pressure supply conduit to said second reservoir; said first pressure regulator comprising an orifice having a predetermined cross sectional area;

said first dispensing conduit for dispensing said first component and said second dispensing conduit for dispensing said second component being separate, so that said components intermix external to said applicator;

said applicator further comprising a first nozzle affixed to said housing and disposed about said first dispensing conduit, and a second nozzle affixed to said housing and disposed about said second dispensing conduit;

said first pressure regulator comprising a pressure regulating valve, and said second pressure regulator comprising a pressure regulating valve.

46. The applicator of claim 45 wherein said first pressure regulating valve is interposed between said first reservoir and the environs external to said applicator and said second pressure regulating valve is interposed between said second reservoir and the environs external to said applicator.

47. The applicator of claim 45 wherein said first pressure regulating valve and said second pressure regulating valve are interposed between said pressure supply and the environs external to said applicator.

* * * * *